United States Patent [19]

Takahashi et al.

[11] 4,236,509
[45] Dec. 2, 1980

[54] CURVING DEVICE IN AN ENDOSCOPE

[76] Inventors: Nagashige Takahashi, Tokiwadai Green Haitsu 602, No. 28-10, Tokiwadai 3-chome, Itabashi-ku, Tokyo; Nobuhiro Noda, No. 1480-33, Kawashima,, Ranzan-machi, Hiki-gun, Saitama, both of Japan

[21] Appl. No.: 852,640

[22] Filed: Nov. 18, 1977

[30] Foreign Application Priority Data

Dec. 28, 1976 [JP] Japan ............ 51/177350[U]

[51] Int. Cl.³ .................................................. A61B 1/00
[52] U.S. Cl. .................................... 128/4; 137/122; 137/134
[58] Field of Search .................. 128/3, 4, 5, 6, 7, 8, 128/2 M, 348, 349 R, 349 B, 349 BV, 350 R, 350 V, 351, 140 R, 188; 138/121, 122, 134, 133

[56] References Cited

U.S. PATENT DOCUMENTS

| | | | |
|---|---|---|---|
| 559,968 | 5/1896 | Brooks | 138/134 |
| 2,448,485 | 8/1948 | Chernack | 138/133 |
| 2,720,221 | 10/1955 | Neilson | 138/133 |
| 3,162,214 | 12/1964 | Bazinet Jr. | 128/4 |
| 3,670,721 | 6/1972 | Fukami et al. | 128/6 |
| 4,098,298 | 7/1978 | Vohrer | 138/122 |

FOREIGN PATENT DOCUMENTS

| | | | |
|---|---|---|---|
| 288854 | 9/1931 | Italy | 138/133 |
| 197275 | 5/1923 | United Kingdom | 138/122 |
| 1383313 | 2/1975 | United Kingdom | 138/134 |

*Primary Examiner*—Robert W. Michell
*Assistant Examiner*—Arthur S. Rose
*Attorney, Agent, or Firm*—Sughrue, Rothwell, Mion, Zinn and Macpeak

[57] ABSTRACT

The curving device in an endoscope is made highly flexible yet resistant to bending. The guide tube of the curving end section is provided with a groove or ring-shaped grooves which are formed respectively spirally or at equal intervals in the outer wall of the guide tube. The coil is made of a wire whose diameter is substantially equal to the depth of the groove or grooves and smaller than the width of the groove or grooves. The coil is fitted into the groove or grooves in a spiral manner.

4 Claims, 4 Drawing Figures

CURVING DEVICE IN AN ENDOSCOPE

BACKGROUND OF THE INVENTION

This invention relates to an improvement of an inner guide tube forming the curving end section, made of a flexible thin tube, of an endoscope, and more particularly to a structure by which the curving characteristic of the guide tube is improved and the collapse or abrupt bend thereof is prevented as much as possible when it is curved.

When the curving end section, made of a flexible thin tube, of an endoscope is inserted into a part of a human body to be examined, it is curved smoothly over a wide range of curve angles according to the conditions of a path to the aimed part of the human body or by an operating means for feeling for the part. For this curving operation, two angle wires connecting a manual operating section to the aforementioned end section are employed. However, if the curving pressure of the curving section is great, the tensions of the angle wires are increased in the curving operation. As a result, the durability of the wires is decreased. Furthermore, if a force for operating the angle wires is increased, it is rather difficult for the operator to feel the contact conditions of the end section with the manual operating section. Therefore, the operability of the endoscope is lowered.

Therefore, in the endoscope of this type, not only the outer pipe of the aforementioned flexible thin pipe but also the inner tube of the same should be so designed as to be readily curved. In order to meet this requirement, the wall thickness of the tube should be made thinner since in such a mechanism it is preferable to make the internal volume of the tube as large as possible and to make the outside diameter thereof as small as possible. If the wall thickness of the tube is merely reduced, however, the tube may be bent when it is curved, which will obstruct the further operation.

In order to overcome this difficulty, two methods have been proposed, in one of which a metallic coil whose diameter is such that the coil can be in close contact with the inner wall of a conventional tube is inserted thereinto, and in the other of which a metallic belt coiled to have a diameter which is substantially equal to the outside diameter of a tube is placed over the outer wall of the tube. However, the former method is not practical, because the internal volume of the tube is decreased, which will obstruct the insertion of forceps or the like, and in addition it becomes difficult to clean the inside of the tube because the inner wall of the tube becomes uneven because of the insertion of the coil, which results in the contamination or infection of bacteria or bacilli. On the other hand, the latter method is also disadvantageous because the tube's outside diameter is increased, and although the bend of the tube may be prevented, it is unsatisfactory in flexibility because the stiffness of the coil is added to that of the tube.

In order to overcome the disadvantage caused by the addition of the coil, there has been proposed a method in which a metallic belt is wound, in a coil state, around the outer wall of a tube and is then embedded in the tube by heat treatment. However, this method is still disadvantageous in that because the metallic belt is embedded in the tube, shrinkage occurs between the tube and the coil, and it is unexpectedly poor in flexibility.

SUMMARY OF THE INVENTION

Accordingly, an object of this invention is to eliminate all of the drawbacks accompanying the conventional end section of the endoscope. The most significant feature of the invention is to fit a coil in a groove or grooves provided in the outer wall of a tube in the end sectin of the endoscope. More specifically, the guide tube of the curving end section is provided with either a spiral groove or a plurality of ring-shaped grooves at equal intervals. The coil is made of hard wire having a diameter substantially equal to the depth of the groove or grooves and smaller than the width of the groove or grooves. The coil is not fixed to the tube so that relative movement can occur therebetween. The structure according to the invention is both highly flexible and resistant to bending.

BRIEF DESCRIPTION OF THE DRAWINGS

The invention will be described in detail with reference to the embodiments as shown in the accompanying drawings, in which.

DETAILED DESCRIPTION OF THE PREFERRED EMBODIMENTS

Figure 1:
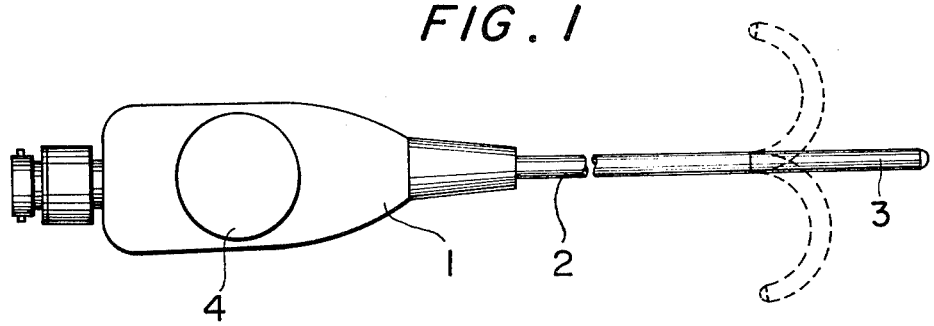
FIG. 1 is a side view illustrating one example of the endoscope.

Referring to FIG. 1, an end section 3 which is inserted into a part to be examined is connected through a flexible connecting pipe 2 to a manual operating section. The end section 3 is elevated upward or downward as viewed in FIG. 1 by turning an operating knob 4 provided on the manual operating section 1.

Figure 2:
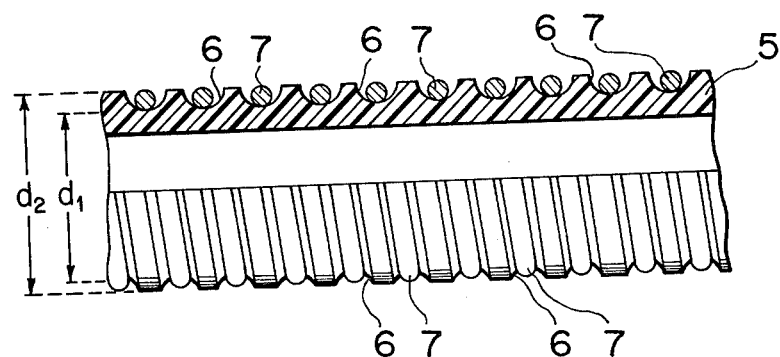
FIG. 2 is an enlarged side view, with its one half cut away, showing essential parts of one embodiment of the device according to the utility model.

FIG. 2 is an enlarged view, with one half cut away, illustrating a part of an inner tube 5 in the end section 3. A groove 6 is spirally formed in the outer wall of the tube 5. A coil 7 is made of a steel wire whose diameter is substantially equal to the depth of the groove 6 but is smaller than the width of the groove 6 (if it is assumed that the groove 6 is a semi-circular groove, the diameter of the steel wire is smaller than the diameter of the semi-circular groove) so that the inner diameter of the wire coil is substantially equal to the inner diameter $d_1$ of the spiral groove and the outer diameter of the wire coil is substantially equal to the outer diameter $d_2$ of the spiral groove. The coil thus formed is fitted into the groove 6.

Figure 3:
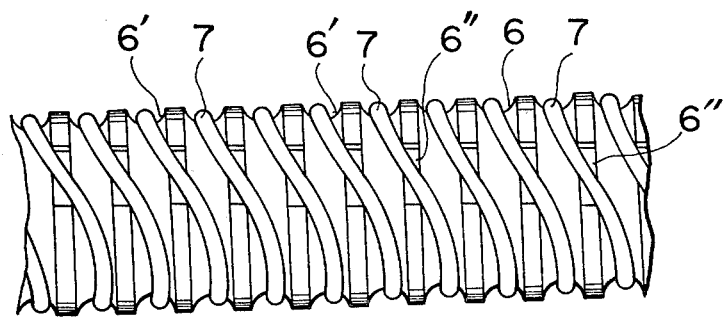
FIG. 3 is an enlarged side view showing essential parts of another embodiment of the device according to the utility model.

FIG. 3 is an enlarged side view showing another embodiment of the tube in the device according to the invention. As shown in FIG. 3, grooves 6' are provided in the outer wall of a tube 6 at a certain interval, and one to several longitudinal grooves 6" are formed in the outer wall of the tube 6 in the longitudinal direciton thereof. The above-described coil 7 are fitted into the grooves 6' through the longitudinal grooves 6" as shown in FIG. 3. The coil 7 may be made of hard synthetic resin or the like instead of steel.

In the device thus constructed according to this invention, the wall thickness of the tube 5 which is a part of the end section 3 and is curved as required is partially thinner because of the provision of the grooves 6, 6' and 6". Therefore, it is obvious that the tube according to the invention can be more readily curved than other tubes which are not provided with grooves. The coil 7 is fitted in the groove 6 or the grooves 6' and 6" in close contact with the bottoms thereof. Therefore, the deformation of the tube is prevented to a great extent, and the collapse or abrupt bend of the tube is prevented. It should be noted that the tube 5 and the coil are not formed into one unit. Therefore, when the tube is curved, the coil 7 is slid along the groove 6 as the wall of the tube is extended or contracted; that is, the tube can be curved smoothly. Thus, the excellent flexibility of the tube 5 due to the thin wall thickness can be maintained.

Figure 4:
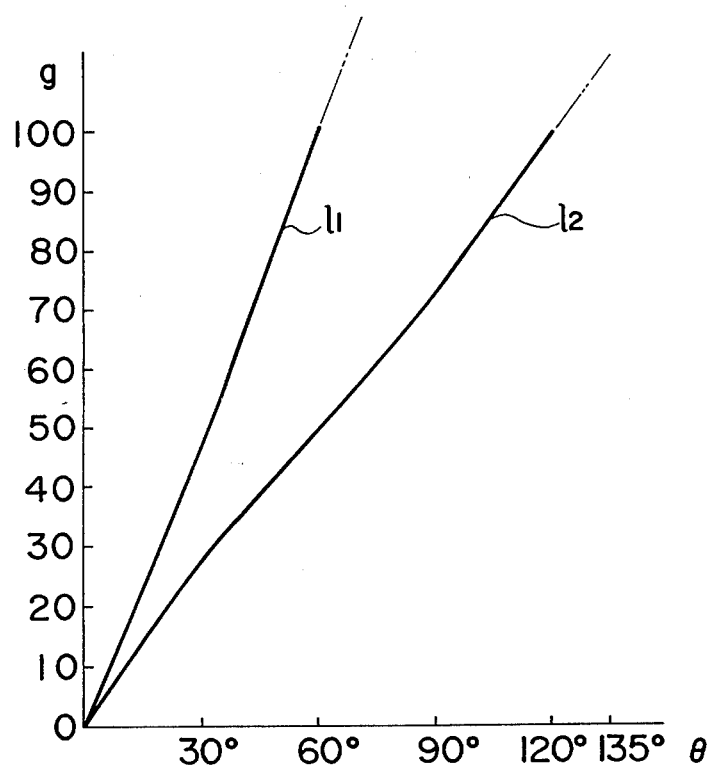
FIG. 4 is a graphical representation indicating a curvature characteristic of an endoscope provided with the device according to the utility model.

FIG. 4 is a characteristic curve diagram with the curve angle Q as the horizontal axis and with the wire tension g as the vertical axis. As is apparent from the comparison between the characteristic curve $l_1$ for the conventional tube only (Teflon, inside diameter 2.5 mm, outside diameter 3.1 mm) and the characteristic curve $l_2$ for the tube according to this invention (the conventional tube being provided with seven to eight grooves per centimeter, the depth of the groove being of the order of 0.1–0.2 mm) with the coil described before, the device according to this invention becomes effective as the curve angle increases.

In addition, as the coil 7 is fitted into the groove 6 formed in the outer wall of the tube in such a manner that the outside diameter is less than the outside diameter of the tube, the outside diameter of the tube is not increased by the addition of the coil. Thus, the device according to the invention is quite practical in use.

What is claimed is:

1. In an endoscope of the type comprising a flexible end section which is inserted into a part to be examined, a manual operating section for controlling the curving of said flexible end section, a flexible connecting pipe connecting said flexible end section to said manual operating section and connecting means in said flexible pipe coupling said manual operating section and flexible end section, the improvement in a curving device for said flexible end section comprising:
 a guide tube having a smooth interior surface and having a groove in the exterior surface thereof, said groove being shaped such that a wire can be fitted into said groove and wrapped around the tube in the form of a coil;
 a hard wire wrapped around said tube and fitted within and in direct contact with the surface of said groove along the length of said tube and forming a coil, the diameter of said wire being substantially equal to the depth and smaller than the width of said groove so that said wire is slidable across the width of said groove during flexing of said tube.

2. The curving device as recited in claim 1 wherein said groove comprises a spiral groove.

3. The curving device as recited in claim 1 wherein said groove comprises a plurality of ring-shaped grooves at spaced intervals along the length of said guide tube and apertures are provided in the walls of the grooves to permit the wire coil to pass between adjacent grooves.

4. The curving device as recited in claim 1 wherein said coil of hard wire is made of steel.

* * * * *